US011918318B2

(12) United States Patent
Matta

(10) Patent No.: US 11,918,318 B2
(45) Date of Patent: *Mar. 5, 2024

(54) MEDICAL TABLE AND SURGICAL DRAPE FOR USE IN SURGICAL PROCEDURES

(71) Applicant: Mizuho OSI, Union City, CA (US)

(72) Inventor: Joel M. Matta, Avon, CO (US)

(73) Assignee: Mizuho OSI, Union City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/125,016

(22) Filed: Mar. 22, 2023

(65) Prior Publication Data

US 2023/0218360 A1 Jul. 13, 2023

Related U.S. Application Data

(63) Continuation of application No. 15/952,207, filed on Apr. 12, 2018, now Pat. No. 11,622,829.

(51) Int. Cl.
| | | |
|---|---|---|
| *A61B 46/20* | (2016.01) | |
| *A61B 46/10* | (2016.01) | |
| *A61B 46/23* | (2016.01) | |
| *A61B 46/27* | (2016.01) | |

(52) U.S. Cl.
CPC .............. *A61B 46/20* (2016.02); *A61B 46/10* (2016.02); *A61B 46/23* (2016.02); *A61B 46/27* (2016.02); *A61B 2046/201* (2016.02); *A61B 2046/205* (2016.02)

(58) Field of Classification Search
CPC . A61B 46/10; A61B 1/00135; A61B 1/00142; A61B 50/00; A61B 46/13; A61B 46/17; A61B 46/30; A61B 46/27; A61B 46/00; A61B 2046/205; A61B 46/20; A61B 2046/201; A61B 46/23; A61F 2013/15073
USPC ......... 600/121, 123–125; 128/845, 849–856; 604/378, 383, 356–357, 327; D24/183–184
See application file for complete search history.

(56) References Cited

U.S. PATENT DOCUMENTS

| | | | | |
|---|---|---|---|---|
| 4,569,341 A | * | 2/1986 | Morris | A61B 46/00 128/853 |
| 4,730,609 A | * | 3/1988 | McConnell | A61B 46/00 128/853 |
| 7,824,353 B2 | | 11/2010 | Matta | |
| 11,622,829 B2 | * | 4/2023 | Matta | A61B 46/23 128/845 |
| 2004/0103904 A1 | * | 6/2004 | Auerbach | A61B 46/27 128/856 |
| 2006/0191540 A1 | * | 8/2006 | Lamprich | A61B 46/23 128/853 |

(Continued)

*Primary Examiner* — Caitlin A Carreiro
(74) *Attorney, Agent, or Firm* — Reed Smith LLP; Matthew P. Frederick; Sidharth Kapoor

(57) ABSTRACT

A surgical drape is disclosed herein that is to be used for medical procedures in order to ensure sterile portions are not contaminated. The surgical drape can be configured to be placed around a surgical site where an operative procedure is to be conducted. The surgical drape includes a u-shaped opening, at least one sleeve, and at least one flap on its proximal end. The at least one sleeve and the at least one flap extend outwardly from a top surface of the drape. The at least one flap includes adhesive components on one side that allow the at least one flap to be folded back on to itself to provide additional protective barrier from contamination.

20 Claims, 17 Drawing Sheets

(56) References Cited

U.S. PATENT DOCUMENTS

| | | | |
|---|---|---|---|
| 2013/0104909 A1* | 5/2013 | Barrier | A61B 46/30 128/852 |
| 2013/0204262 A1* | 8/2013 | Menendez | A61B 17/02 606/89 |
| 2013/0247921 A1* | 9/2013 | Dye | A61B 46/00 128/853 |
| 2014/0138270 A1 | 5/2014 | Ghosh | |
| 2014/0318551 A1* | 10/2014 | Daly | A61B 46/23 128/853 |
| 2016/0008072 A1 | 1/2016 | Pecora | |

\* cited by examiner

MEDICAL TABLE AND SURGICAL DRAPE FOR USE IN SURGICAL PROCEDURES

CROSS-REFERENCE TO RELATED APPLICATION

This application is a continuation of U.S. patent application Ser. No. 15/952,207, filed Apr. 12, 2018, the entire contents of which are incorporated by reference herein.

BACKGROUND

Recent advances in surgery focus on minimally invasive techniques, which utilize smaller and/or a fewer number of incisions, and can eliminate the need in previous techniques to detach or sever muscular tissue. For example, minimally invasive hip replacement surgery utilizes entry at the anterior of the leg of a patient. This point of entry allows a surgeon to perform a hip replacement procedure while only making a single incision of about four inches in length, rather than multiple incisions or incisions of ten inches in length as in prior procedures. Further, muscles within the leg are not damaged through detachment or severing in these procedures, resulting in a much faster recovery time. These procedures still require access to the acetabulum, which must be reamed before insertion of the prosthesis. Further, proper manipulation and positioning of the femur is essential in carrying out the anterior approach hip replacement surgery.

SUMMARY

Disclosed herein is a u-style drape that covers a torso and/or a head portion of a patient. During use of this first u-style drape, wherein the surgical site is located, a second u-style drape is placed over or under this first u-style drape. Unlike the first u-style drape, the second u-style drape covers the patients waist, both legs, and feet. The two drapes overlap, with the u-shape of both the drapes intersecting at the surgical site. The two drapes are aligned and positioned by a user such as a physician to provide access through the drapes to the linear incision length needed for the particular surgery. In one embodiment, the drape disclosed in the present application is symmetrical along the longitudinal center line so it can be used for either left hip or right hip surgery.

In one example embodiment of the drape, the drape may comprise a top surface and an opposite bottom surface; wherein the bottom surface is configured to contact a first user (i.e., a patient), and the top surface is configured to engage with a second user (i.e., a physician). The drape may further comprise at least one sleeve extending perpendicularly from the top surface. The at least one sleeve, which is sealed to separate the top surface of the drape from the bottom surface of the drape, may further include an opening extending from the bottom surface to an interior of the at least one sleeve. The drape may further comprise at least one flap extending perpendicularly from the top surface, wherein the at least one flap is configured to form a secondary barrier by wrapping around a first device and the at least one sleeve. The first device may be a femoral support hook. The drape may further comprise a first opening corresponding to an incision site, wherein the first opening may be in a u-shape configuration or in a window cut-out configuration.

In one example embodiment, a method of packaging a drape is disclosed. The drape may be packaged by folding the drape that includes at least the components described herein.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown. In the drawings.

DETAILED DESCRIPTION

Figure 1:
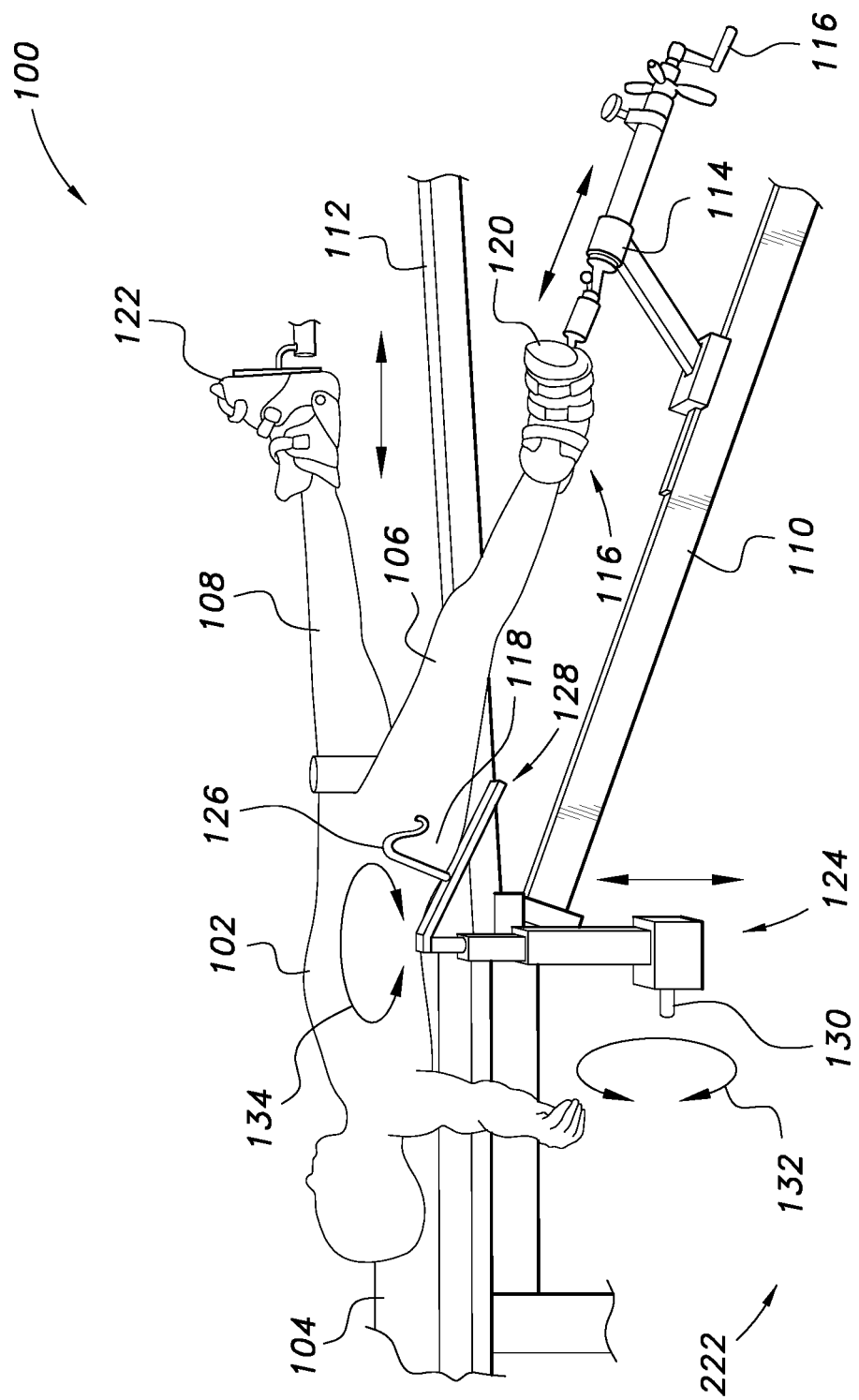
FIG. 1 is a perspective view of a medical table illustrating a patient positioned on the table.

While systems, apparatus and methods are described herein by way of examples and embodiments, those skilled in the art recognize that the systems, apparatus and methods of the presently disclosed technology are not limited to the embodiments or drawings described. It should be understood that the drawings and description are not intended to be limited to the particular form disclosed. Rather, the inventive concepts cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to. Unless specifically set forth herein, the terms "a," "an" and "the" are not limited to one element but instead should be read as meaning "at least one." The term "actuator" is broadly defined herein to mean any component capable of at least initiating movement or control of a mechanism or system, and includes a trigger, a button, a switch or any other enabling device. The terminology includes the words noted above, derivatives thereof and words of similar import.

Referring to the drawings in detail, wherein like numerals indicate like elements throughout, one embodiment of the presently disclosed technology is directed to a medical table and a surgical drape for use in surgical procedures, wherein the surgical drape used by a surgeon during a surgical procedure prevents or avoids sterile portions from becoming non-sterile or contaminated. The sterile portions may include portions of the surgical drape, the medical equipment (i.e., catheters, cutters, brackets, etc.) used for the surgery, and the desired surgical site of the surgical procedure. The term "patient" is broadly defined herein to include human patients of all sizes, genders and demographics, as well as animals (e.g., for veterinarian purposes).

FIG. 1 illustrates a perspective view of a medical table with a patient positioned on the table. A patient 102 undergoing a knee or hip arthroplasty surgery typically will be anesthetized for surgery then placed on the surgical table 100. The back of the patient will be placed on a platform portion 104 of the table, with the legs 106, 108 of the patient being placed over the spars 110, 112 of the table. Each spar has a traction system 114 (not shown for the left leg) for receiving a foot of the patient and holding that foot in a desired position. The traction system can have a traction setting mechanism 116 for applying a desired amount of force on the foot of the patient. The hip 118 of the patient is placed adjacent to a pivot connection between the platform portion 104 and the spars 110, 112 in order to allow the legs of the patient to be moved into a position appropriate for surgery, such as for anterior approach hip surgery. In this figure, the patient is positioned for surgery on the hip associated with right leg 106. Traction boots 120, 122 can be used to ensure traction via the traction system. A manual or electrically powered surgical table jack 124 can be used to raise and lower a femoral support hook 126. The femoral support hook 126 being connected to the table jack 124 by an angled bracket 128. The manual or electrically powered surgical table jack 124 may also correspond to a femur lift mechanism.

The raising and lowering of the jack 124 can be accomplished via the rotation or a rotatable shaft 130, the motion of which is indicated by directional arrow 132. The angled bracket 128 is also capable of rotating relative to the jack 124, such that the surgeon performing the surgery can rotate the hook 126 into and out of position, providing complete control of the positioning of the angled bracket 128 relative to the femur of the right leg 106. The end portion of the hook 126 being shaped to receive and support the femur during the procedure. An appropriate hook is described in U.S. patent application Ser. No. 10/930,809, entitled "Surgical Support for Femur," to Joel M. Matta et al., filed Sep. 1, 2004, issued as U.S. Pat. No. 7,824,353, which is hereby incorporated herein by reference. There can be a hook and corresponding components on each side of the table, one for each leg, in order to allow for operation on either side of the patient.

In operation, the surgeon places a base portion of the femoral support hook 126 into an appropriate opening on the angled bracket 128. The angled bracket 128 has a plurality of openings for receiving the base portion, in order to position the receiving end of the femoral support hook 126 at an appropriate distance from the femur to be supported. At the proper time after an incision is made in the patient, the femoral support hook 126 on the appropriate side can be swung into position in the wound at the hip region of the patient, and can be positioned to support the femur. The surgeon (or an assistant) then can adjust the jack 124 to properly angle and support the femur such that the surgeon can gain unrestricted access to the acetabulum and other portions of the hip in order to accomplish, for example, an artificial hip replacement for the patient. When the support of the femur is no longer needed, the support including the femoral support hook 126 can be lowered using the jack 124, and then swung from the wound in the patient and moved outwardly by the rotation of the angled bracket 128 relative to the jack 124, as shown by directional arrow 134. The angled bracket 128 then can be removed or left in this position as surgery progresses and is finished.

Figure 2:
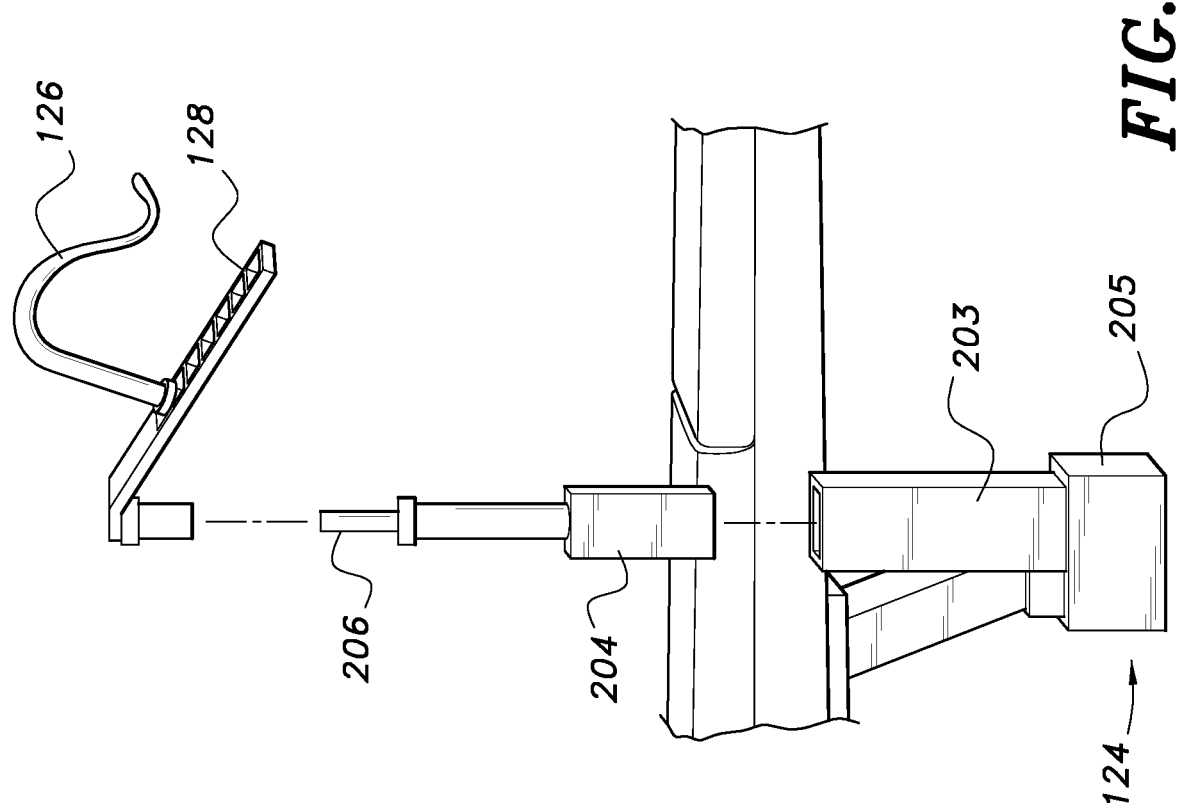
FIG. 2 is a perspective view of a portion of the medical table of FIG. 1 showing the detail of the femoral support hook.

Now referring to FIG. 2, a perspective view of the femoral support hook 126 used in the medical table of FIG. 1 is described. A femoral support hook 126 can be positioned on either side of the table 100 for supporting a respective femur. The femoral support hook 126 can be attached via an angled bracket 128 to an appropriate vertical positioning system or lift, such as a motorized jack 203. Such a surgeon-controlled femoral power lift can enable hyperextension of the hip for improved surgical access. Proper placement allows the surgeon to effect hip replacement without the femur obstructing access to the acetabulum of the hip. The vertical positioning system can include a base portion designed to attach to the table, or to be fixedly positioned with relation to the table. Although a manual jack of the type described in connection with FIG. 1 may also be used, an advantage to using a motorized jack 203 is that the surgeon can control the jack directly, such as through use of a remote control device, which can avoid any potential communication problems between the surgeon and an assistant turning a crank for a jack in previous systems.

Motorized jacks, which can be controlled by the surgeon through a base control unit, a remote control unit, or a foot pedal, can be used to raise and lower the appropriate femoral support hook 126. Each angled bracket 128 can be rotated relative to the respective jack 124 and the respective motorized jack 203 such that the surgeon performing the surgery can rotate the hook into and out of position, providing complete control of the positioning of the femoral support hook 126 relative to the femur. The motorized jack 203 and control mechanism can include any appropriate devices known or used in the art for imparting a controlled amount of linear motion. As seen in the embodiment of FIG. 2, one embodiment of the jack 124 can include a telescoping member 204 controlled by a rotary drive motor 205, and a square shaped post 206 that extends from the telescoping member 204. The post 206 is configured to engage with a metal sleeve of the angled bracket 128 such that the angled bracket 128 is affixed and/or snap-fitted on to the post 206 for use during a surgical procedure. This metal sleeve of the angled bracket 128 extends over the square post 206 and covers the respective sleeve 304A, 304B (discussed below). One skilled in the art would appreciate that when prepared for surgery, the femoral support hook 126 and the angled bracket 128 may be sterile, whereas the motorized jacket 203, the telescoping member 204, square shaped post 206 may not be sterile.

In alternative embodiments, the position of the femoral support hook 126 in the angled bracket 128 and/or the rotation of the angled bracket 128 can be accomplished through sliding mechanisms, or can be automated through use of a motorized device. These adjustments then could be accomplished by the appropriate control mechanism available to the surgeon and/or assistant.

In operation, the surgeon can place a base portion of the femoral support hook 126 into an appropriate opening on the angled bracket 128. The angled bracket 128 has a plurality of openings for receiving the base portion of the femoral support hook 126, in order to position the receiving end of the femoral support hook 126 of the femur at an appropriate distance from the femoral support hook 126 to be supported. At the proper time after an incision is made in the patient, the femoral support hook 126 on the appropriate side can be swung into position in the wound at the hip region of the patient, and can be positioned to support the femur. The surgeon (or an assistant) can then cause the jack 124 to properly angle and support the femur, by operating a foot pedal or control mechanism (not shown) as discussed above, such that the surgeon can gain unrestricted access to the acetabulum and other portions of the hip in order to accomplish an artificial hip replacement for the patient.

Figure 3:
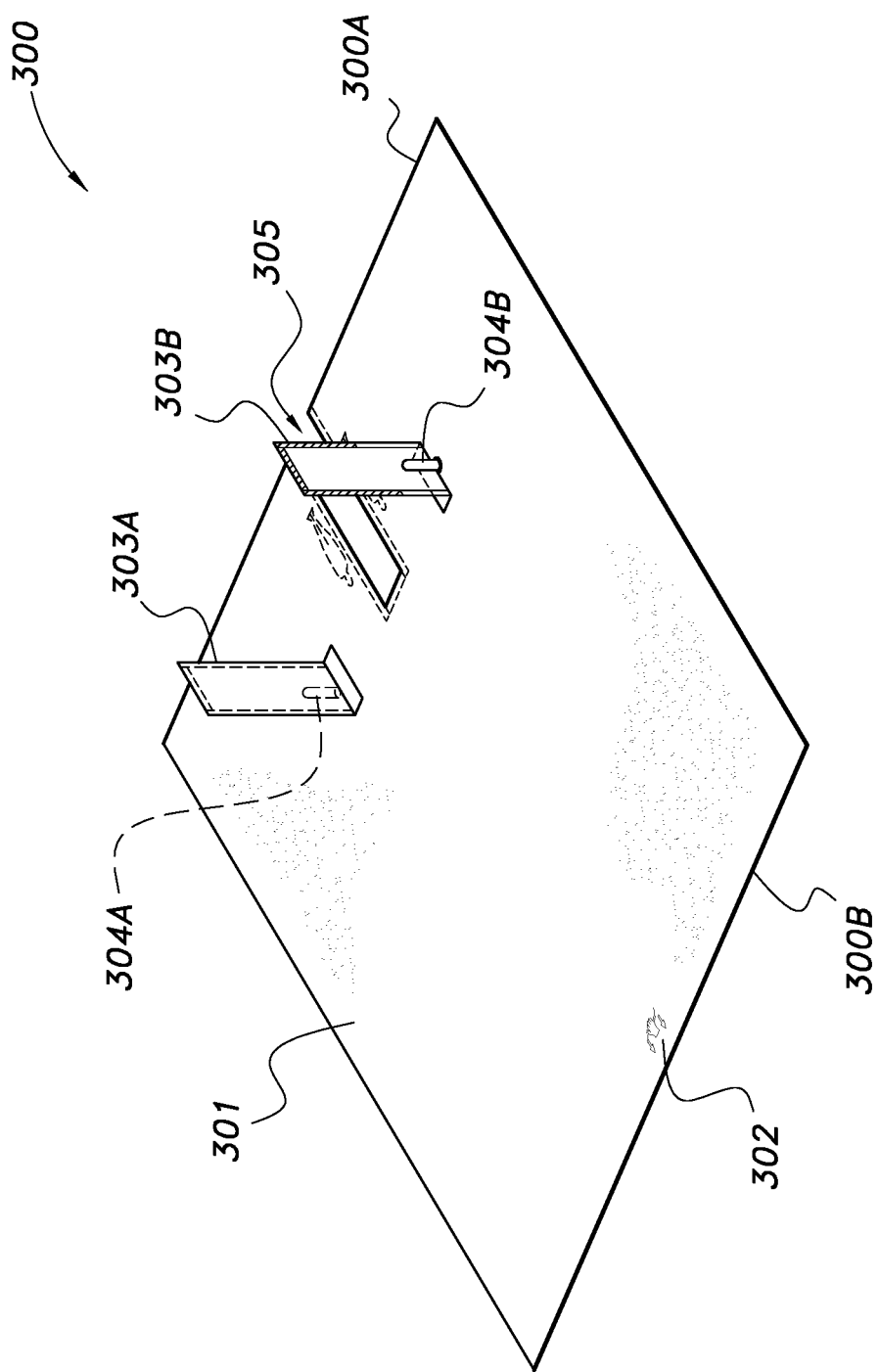
FIG. 3 is a perspective view of a top side or surface of an embodiment of drape.

Next, referring to FIG. 3 a perspective view of a top side or surface 301 of one embodiment of a surgical drape 300 is shown that is configured to be used with a surgical table 100 shown in FIG. 1 and FIG. 2. The drape 300 is shaped and sized to cover at least a torso and a head portion of a patient. In this embodiment, the top surface 301 of the surgical drape 300 is generally rectangular in shape with a proximal end 300A and a distal end 300B, and with varying width and length dimensions. One skilled in the art would appreciate that the surgical drape 300 may not be limited to a rectangular shape and in other embodiments may take other configurations such as a square shape. During use, the top surface 301 is the surface that is facing and may be in contact with the physician or surgeon performing the surgical procedure. The top surface 301 may include the following: a u-shaped opening 305; at least one flap 303A, 303B; at least one sleeve 304A, 304B; and at least one marking 302. Wherein, the u-shaped opening 305; the at least one flap 303A, 303B and the at least one sleeve 304A, 304B are by the proximal end 300A of the top surface 301 of the drape 300; and the at least one marking 302 is by the distal end 300B of the top surface 301 of the drape 300. The top surface 301 includes a u-shaped opening 305 on its proximal end 300A. The u-shaped opening 305 corresponds to the incision site as to where a physician will make an incision for purposes of performing a surgical procedure. The u-shaped opening 305 allows for the physician to perform its desired surgery by maneuvering his or her surgical tools in and around the u-shaped opening 305. The drape 300 may be used in conjunction with a second drape (not shown) having a u-shaped opening. The second drape may cover the remaining exposed portion of the patient's legs, with the u-shaped portion of the second drape overlapping the u-shaped portion of the drape 300. By adjusting the location of the second drape, the portion of the patient that is exposed by the intersecting u-shaped cutouts may be increased or decreased based on the needs of the surgeon.

One skilled in the art would appreciate that the u-shaped opening 305 is for illustrative purposes only. In an alternative embodiment, the drape may be sized to cover the full body of the patient. In these embodiments, rather than a u-shaped opening 305, the drape may include a window. The drape 300 could be configured to have a surgical site opening similar to the opening disclosed in U.S. patent application Ser. No. 15/912,530, filed on Mar. 5, 2018, which is incorporated herein by reference. Alternatively, the drape 300 could be configured such that the drape 300 covers a lower portion of a patient, and the u-shaped opening 305, the at least one flap 303A, 303B; and the at least one sleeve 304A, 304B are oriented accordingly in an orientation that is reversed from the one described above. Regardless, the u-shape design should allow a surgeon, for example, to easily configure the opening in the drapes to match the size of the surgical site, for example as discussed in U.S. patent application Ser. No. 15/912,530, filed on Mar. 5, 2018.

Still referring to FIG. 3, the top surface 301 of the drape 300 includes at least a first flap 303A, a second flap 303B, a first sleeve 304A and a second sleeve 304B. These aforementioned features are positioned by the proximal end 300A of the drape 300 and adjacent to the u-shaped opening 305. As shown in FIG. 3, the first and second sleeves 304A, 304B and the first and second flaps 303A, 303B, may extend or protrude generally perpendicularly outward from the top surface 301. The first and second sleeves 304A, 304B and the first and second flaps 303A, 303B are flexible such that they can be maneuvered, placed, bent or wrapped around another object. One skilled in the art would appreciate that the first and second sleeves 304A, 304B are sterile barriers to the femur lift mechanism or jack 124 (shown in FIG. 2).

The first sleeve 304A may have a height that is the same, similar or different to a height of the second sleeve 304B. Likewise, the first flap 303A may have a height that is the same, similar or different to a height of the second flap 303B. However, height of the first and second flaps 303A, 303B may be greater than the height of the first and second sleeves 304A, 304B, as shown in FIG. 3. The first and second flaps 303A, 303B may extend beyond the height of the first and second sleeves 304A, 304B. With respect to the positioning of these features, as shown in FIG. 3, the first flap 303A is positioned in front of the first sleeve 304A such that the first flap 303A in a sense obstructs the first sleeve 304A from the u-shaped opening 305. Similarly, the second flap 303B is positioned in front of the second sleeve 304B such that the second flap 303B in a sense obstructs the second sleeve 304B from the u-shaped opening 305. The first flap 304A and the second flap 304B are spaced apart on the top surface 301 and are generally adjacent to, and separated by, the u-shaped opening 305 as shown.

Lastly, FIG. 3 shows at least one marking 302 on a distal end 300B of the top surface 301 of the drape 300. The marking 302 may represent a hand symbol that is holding the top surface 301 of the drape 300 and the direction of arrows which instruct a physician or user to pull the drape 300 in a certain direction. For example, marking 302 illustrates direction of arrows in one direction that instructs the physician how to unfold the drape 300 once taken out of its packaging.

Figure 4:
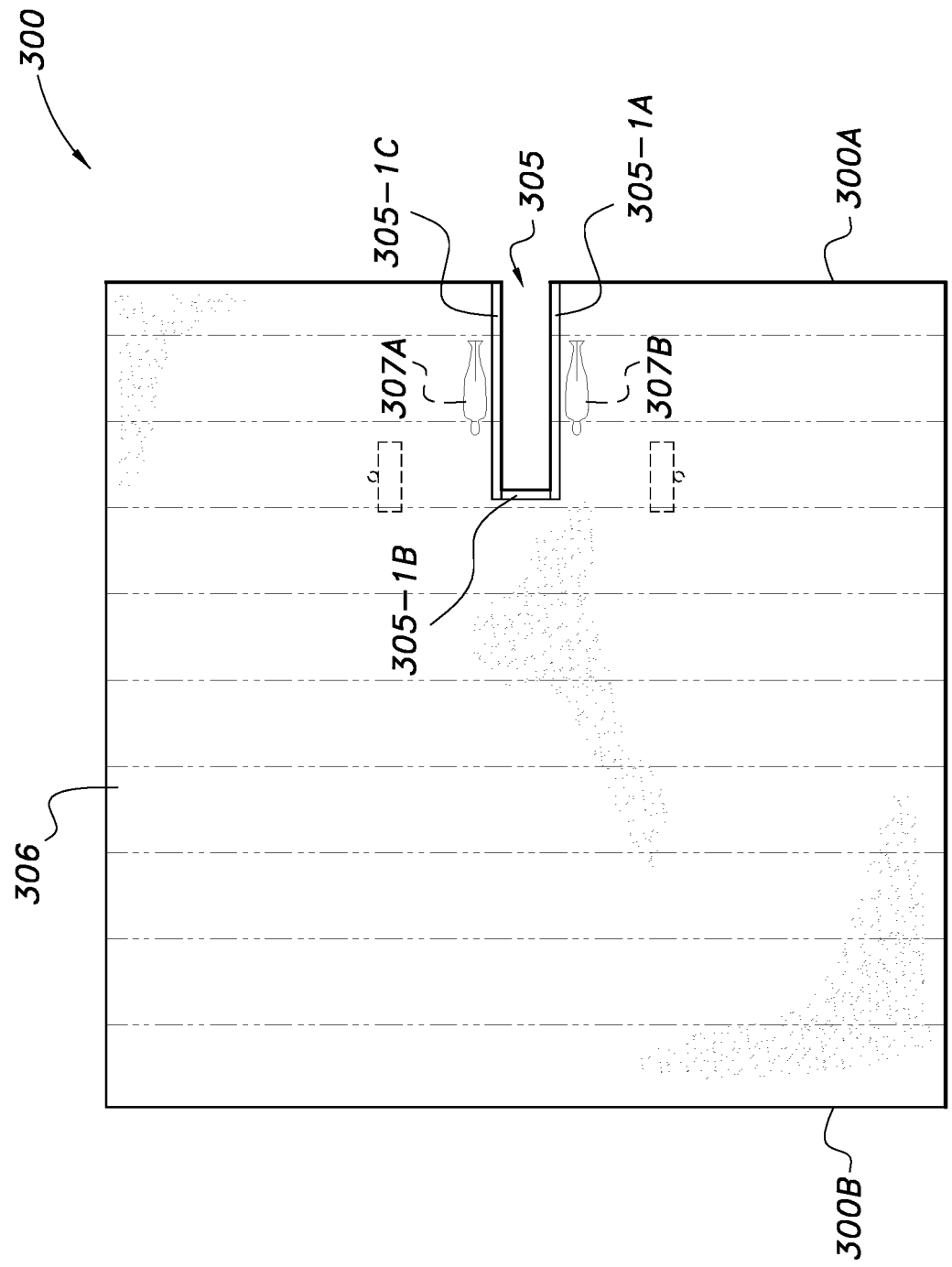
FIG. 4 a perspective view of a back side or surface of an embodiment of a drape.

Next, referring to FIG. 4, a perspective view of an embodiment of a back side or surface 306 of a surgical drape 300 is shown. The back surface 306 of the drape 300 is opposite to the top surface 301 of the drape 300 as shown in FIG. 3. During use, the back surface is the surface that is facing and/or in contact with the patient. The back surface 306, unlike the top surface 301, includes at least two markings 307A, 307B, in addition to the u-shaped opening 305. These markings 307A, 307B represent the orientation of the patient that should be observed with respect to placing the drape 300 on the patient. For example, as shown in markings 307A, 307B, which depicts a patient, for example, has its head facing the distal end 300B and feet facing the proximal end 300A. Such markings allow the physician to orient the drape 300 accordingly during the surgical procedure. As shown in FIG. 4, the markings 307A, 307B are located on either side of the u-shaped opening 305. One skilled in the art would appreciate that the markings 307A, 307B disclosed herein are not limited to such representation, and similar representations may be undertaken. The u-shaped opening 305 on the bottom surface 306 of the drape 300 may include an adhesive tape 305-1A, 305-1B and 305-1C. These are positioned around the edges of the u-shaped opening 305 such that upon use of the drape the adhesive tape 305-1A, 305-1B, 305-1C can be affixed to a patient's skin prior to surgery. Thereby, ensuring that the drape 300 is in place and does not move or reposition during a surgical procedure. In order to apply the adhesive tape 305-1A, 305-1B, 305-1C to a patient's skin, a protective outer covering may be first removed such that the underlying adhesive surface is exposed in order to firmly secure the drape 300 to the patient's skin.

Figure 5:
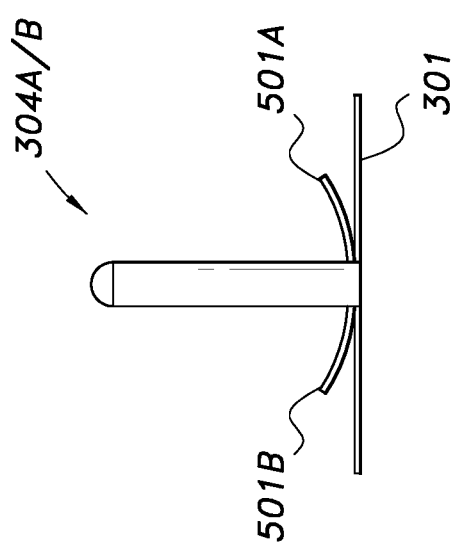
FIG. 5 illustrates a first or a second sleeve that extends or protrudes outwardly from the top surface of the drape.

Now FIGS. 5 and 6 will be discussed in detail. FIG. 5 illustrates a first or a second sleeve 304A, 304B that extends or protrudes generally outward from the top surface 301 of the drape 300. The first and second sleeve 304A, 304B include a hollow interior or cavity that extends through the length of the respective sleeve. Referenced in conjunction with FIG. 4, the hollow cavity extends from the bottom surface 306 of the drape 300 to the length of the respective sleeve 304A, 304B, but is fully sealed in that the sleeve 304A, 304B forms a sterile barrier between the bottom surface 306 of the drape 300 and the structure placed inside of the sleeve 304A, 304B, and the top surface 301 of the drape 300. This hollow cavity allows for the respective sleeve 304A, 304B to be inserted or affixed to the square or rectangular shaped post 206 shown in FIG. 2 such that the base of the respective sleeve is roughly co-planar to the top surface of the post 206.

In further embodiments, the first and second sleeve 304A, 304B include one or more tabs or handles 501A, 501B. In one embodiment, the first and second handles 501A, 501B extend from the base of the respective sleeve 304A, 304B in an outward direction with free ends. The interior portion of the first and second handles 501A, 501B are affixed at or near the base of the respective sleeve 304A, 304B, but have distal free ends that are not connected to the top surface 301 of the drape 300. The handles 501A, 501B are made of a somewhat rigid material, while the drape 300 and sleeve 304A, 304B are made of a somewhat more flexible material. The distal free ends of the first and second handles 501A, 501B are configured to be engaged by a user such that the respective sleeve 304A, 304B can be inserted or affixed to the square shaped post 206 shown in FIG. 2. The rigid nature of the handles 501A, 501B may make it easier for the user to grasp and apply sufficient force and direction to guide the sleeve 304A, 304B over the post 206 without ripping or otherwise damaging the drape or sleeve. It is noted that handles 501A, 501B in FIG. 5 are shown in a curve shape only for illustration purposes, however, the handles 501A, 501B may be flat, curved, or in any other configuration to assist the user in grasping the handles 501A, 501B. Further, handles 501A, 501B may be a single continuous piece or at least two separate pieces that are affixed to the respective sleeve 304A, 304B.

Figure 6:
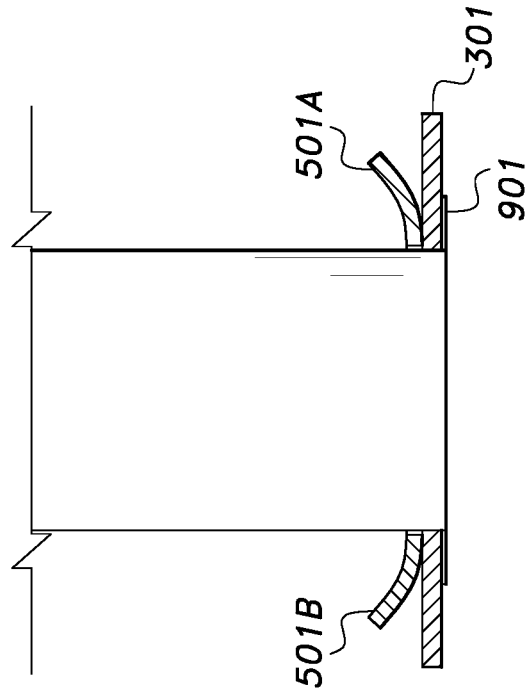
FIG. 6 represents a closer view of the sleeve shown in FIG. 5.

FIG. 6 represents a closer view of the sleeve shown in FIG. 5. In addition to handles 501A, 501B, a flange 901 is illustrated in FIG. 6. The flange 901 may be an extended portion of the sleeve 304A, 304B, or may be a separate annular piece, that is positioned on the bottom surface 306 of the drape 300 opposite to the hollow interior cavity of the respective sleeve 304A, 304B. The flange 901 may be bonded to the bottom surface 306 of the drape 300 using pressure sensitive adhesive, heat seal adhesive and/or ultrasonic sealant. Thereby, securing the sleeve 304A, 304B on the bottom surface 301 of the drape 300. Such securing mechanism provides strain relief to help prevent a tear or rip in the drape 300, especially around regions of the respective sleeve 304A, 304B when the respective sleeve 304A, 304B is being inserted or affixed to the square shaped post 206. The flange 901 may be further affixed to the bottom surface of the drape 306 by an additional annular layer of adhesive covering the flange 901.

Figure 7:
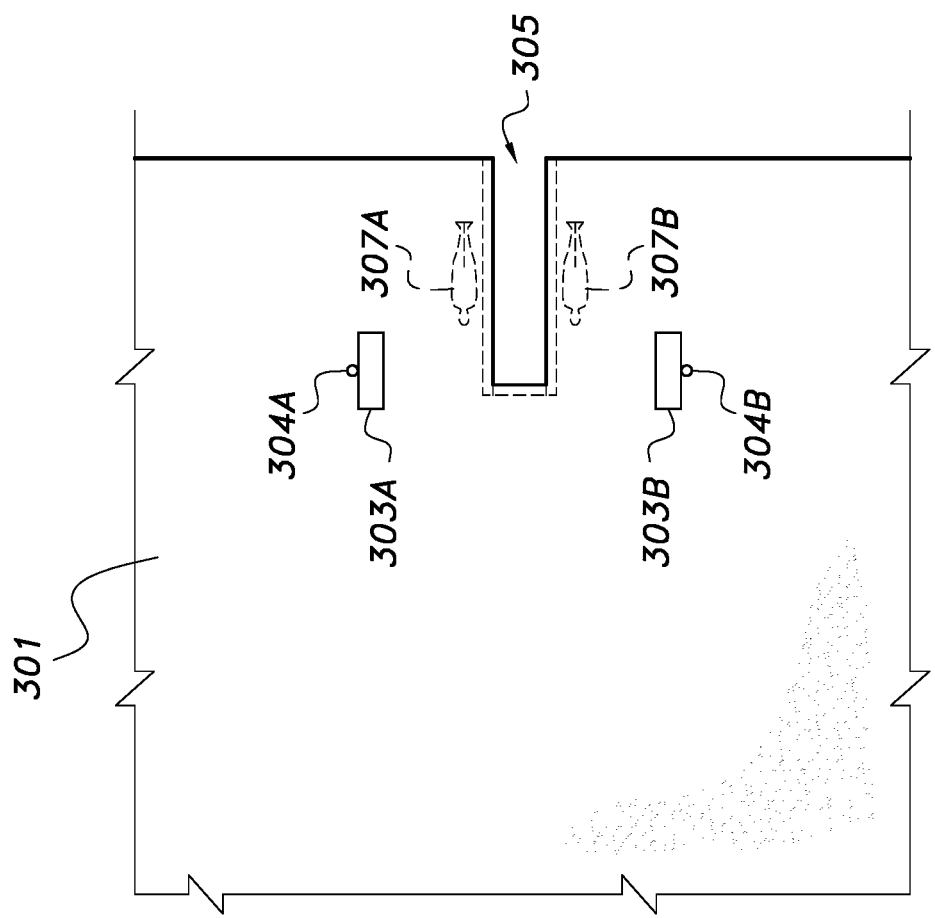
FIG. 7 illustrates a top view of the top surface in one embodiment of the drape.

Next referring to FIG. 7, a top view of the top surface 301 of an embodiment of the drape 300 is illustrated. As shown in FIG. 7, same components as discussed above are included on the top surface 301 of the drape 300. That is, as discussed before, the top surface 301 includes the following—a first flap 304A, a second flap 304B, a first sleeve 304A, a second sleeve 304B, and a u-shaped opening 305. Further, as represented by dotted lines, markings 307A, 307B are illustrated that are on the bottom surface 306 of the drape 300.

Figure 8:
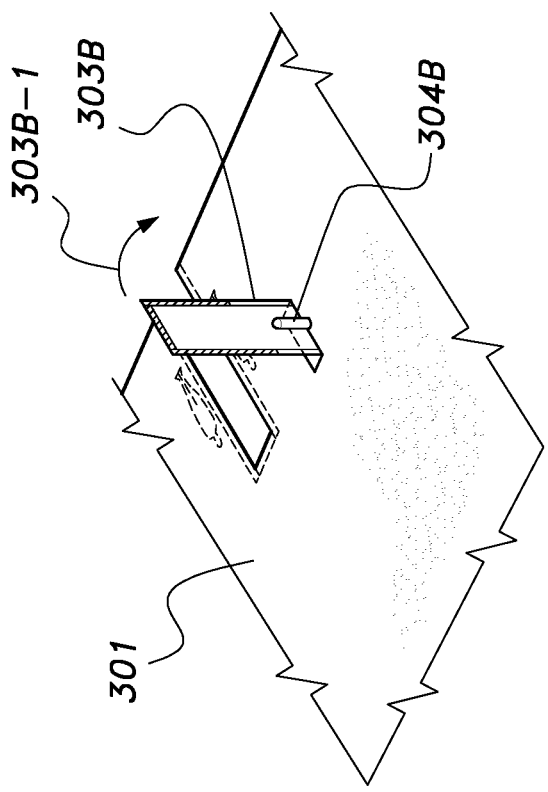
FIG. 8 illustrates a cut out or a segment of the top surface of an embodiment of the drape.

Next, FIGS. 8 and 9 will be discussed. FIG. 8 illustrates a cut out or a segment of the top surface 301 of one embodiment of the drape 300, wherein only the second sleeve 304B and the second flap 303B are shown. As shown in FIG. 8, and discussed previously, the second sleeve 304B and the second flap 303B extend or protrude generally perpendicularly from the top surface 301 of the drape 300. The flaps 303A or 303B may act as a secondary sterile barrier in case the respective sleeve 304A, 304B or the attachment of the respective sleeve 304A, 304B to the drape 300 is breached during installation of the angled bracket 128 or otherwise compromised by accidental pulling or tugging of the drape 300.

Figure 9:
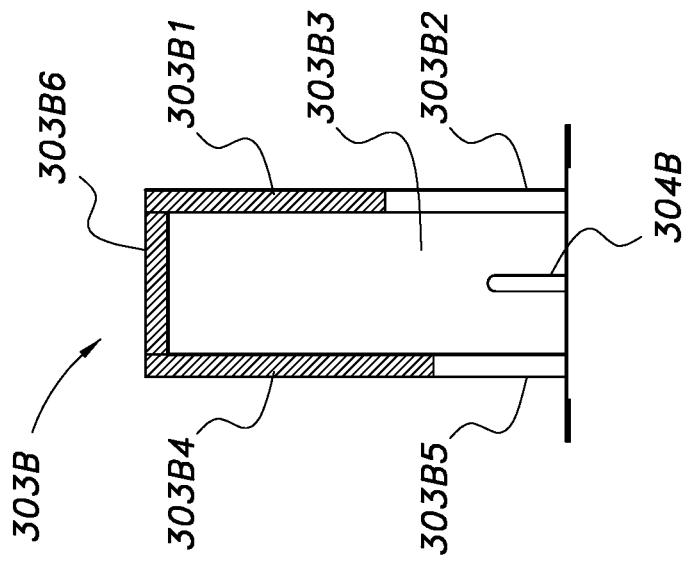
FIG. 9 illustrates a detailed view in one embodiment of a flap and a sleeve.

FIG. 9 illustrates an embodiment showing a detailed view of the second flap 303B and the second sleeve 304B. As shown in FIG. 9, the second flap 303B is generally perpendicular to the top surface 301 of the drape 300, and includes three sides. The three sides may form a shape of a rectangle or may have a similar configuration as appreciated by one skilled in the art. The sides or edges of the second flap 303B are represented as 303B1, 303B2, 303B4, 303B5 and 303B6. The middle section of the second flap 303B that forms the body of the same is represented as 303B3. The side or edge 303B4, 303B5 is parallel to the side or edge 303B1, 303B2. The side or edge 303B6 is perpendicular to the sides 303B4 and 303B1 as shown in FIG. 6. In particular, sides or edges 303B4, 303B6 and 303B1 may have adhesive tape positioned on them. When ready to be used, a user, such as a physician or technician, may remove a protective outer covering from the adhesive tape such that underlying adhesive surface is exposed. The protective outer covering protects the adhesive surface from sticking to unwanted surfaces prior to when the drape 300 is ready for use.

It is important to note, as shown in FIG. 9, that in certain embodiments, the length of the adhesive tape on the edge 303B4 may be longer than the length of the adhesive tape on the edge 303B1. As illustrated further in FIG. 16F (discussed below), the second flap 303B is folded back on itself as indicated by arrow 303B-1 (shown in FIG. 8). The folding back of the second flap 303B results in—(i) the edge 303B4 folding back on itself to form a second barrier on the drape 300 and the angled bracket 128 as the adhesive tape on the edge 303B4 attaches to itself and/or to the drape 300; (ii) the edge 303B1 folds back on itself to form a second barrier on the angled bracket 128 and the drape 300 as the adhesive tape on the edge 303B1 attaches to itself and/or the drape 300; and (iii) the adhesive tape on the edge 303B6 attaches to the drape 300. The edges represented by 303B5 and 303B2 are edges of the second flap 303B that do not include adhesive tape. As illustrated further in FIG. 16F (discussed below), part of the angled bracket 128 extends through the respective flap 303A, 303B, and part of the angled bracket 128 is covered by the respective flap 303A, 303B.

It is noted that the above discussion is made with respect to the second flap 303B; however, same features, orientation and components also similarly apply to the first flap 303A. One skilled in the art would appreciate to interpret the first flap 303A having the same features as the second flap 303B. Further, one skilled in the art would appreciate that the respective flaps 303A, 303B are used depending on which hip is being operated. For example, if a left hip is being operated, the second flap 303B may be used, and if a right hip is being operated, the first flap 303A may be used. The use of two different flaps 303A, 303B, allows the surgeon to use the drape 300 either for a right hip surgery or a left hip surgery. However, the drape 300 may only be used for a single procedure at a time. That is, either performing a right hip surgery or a left hip surgery. As such, certain example embodiments of the drape 300 may include only a single flap and a single sleeve for use in a specific hip (right or left) surgery.

Figure 11:
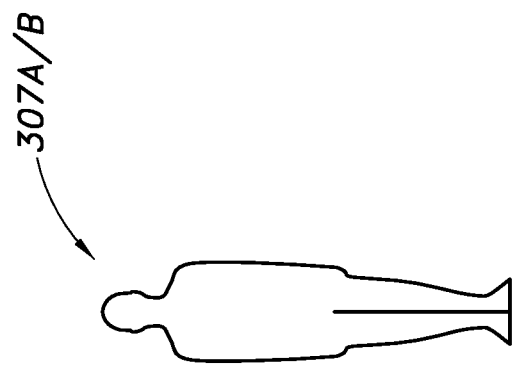
FIG. 11 illustrates a different type of marking that is represented on a bottom surface in one embodiment of the drape.
Figure 10:
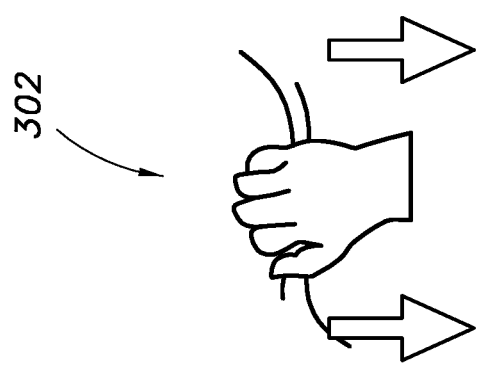
FIG. 10 represents a marking positioned on top surface in one embodiment of the drape.

Now referring to FIGS. 10 and 11. FIG. 10 represents a marking positioned on top surface 301 of an embodiment of the drape 300 by the distal end 300B of the drape. As discussed above with respect to FIG. 3, the marking 302 may represent a hand symbol that is holding the top surface 301 of the drape 300 and the direction of arrows which instruct a physician or user to pull the drape 300 in a certain direction. For example, marking 302 illustrates direction of arrows in one direction that instructs the physician how to unfold the drape 300 once taken out of its packaging. One marking 302 is shown in the figures, however, one skilled in the art would appreciate that multiple markings of similar character or representation may be undertaken.

Referring to FIG. 11, in certain embodiments, a different type of marking 307A, 307B is represented. As discussed above with respect to FIG. 4, markings 307A, 307B represent the orientation of the patient that should be observed with respect to placing the drape 300 on the patient. Discussion set forth above with respect to FIG. 4 is reiterated here. One skilled in the art would appreciate that the markings 307A, 307B disclosed herein are not limited to such representation, and similar representations may be undertaken.

Figure 13:
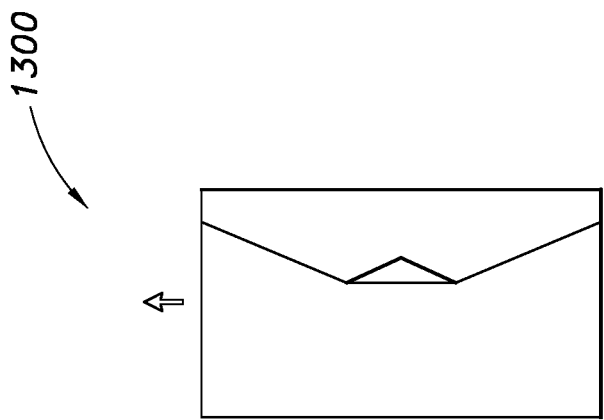
FIG. 13 represents an embodiment including a folded configuration of the drape that is inserted inside the package shown in FIG. 12.
Figure 12:
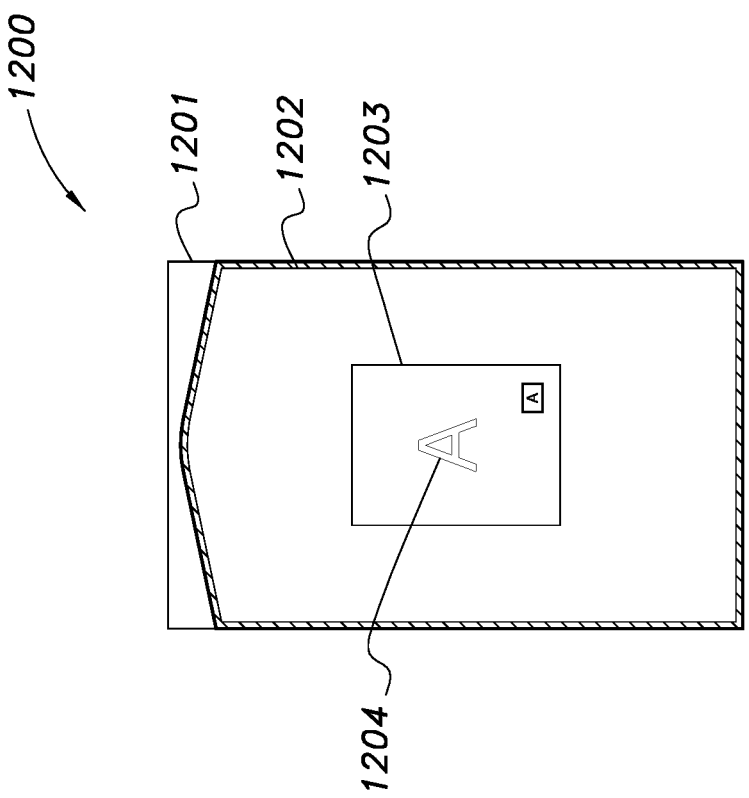
FIG. 12 represents an example embodiment of a package.

Next, FIGS. 12 and 13 will be discussed. FIG. 12 represents an embodiment of the final package that may be manufactured as an end product. The package 1200 includes the drape 300 in a folded configuration that is protected by an outer envelope as represented by 1300 shown in FIG. 13 in order to protect or maintain the sterility of the drape 300 as it is deployed from a folded configuration. That is, the drape 300 in a folded configuration with an outer envelope, represented as 1300, is positioned or placed inside the package 1200 before being shipped or sold to a final user or customer. One skilled in the art would appreciate that the entire drape 300, the outer envelope 1300, and the inside of the package 1200 may be made sterile before being shipped or sold. The arrow represented in FIG. 13 illustrates the removal of the folded drape 1300 from the package 1200.

In certain embodiments, the package 1200 may be a chevron pouch. One skilled in the art would appreciate that a chevron pouch is a type of device packaging that features an entire peel-able side 1202 with a seal shaped like a chevron 1201. It is used most often for sterile medical products that do not require rigid packaging. Use of chevron package prevents sterile components from becoming non-sterile. The package 1200 may further include a label 1203 with instructions of use 1204. The instructions of use 1204 inform a user how to use the drape 300. One skilled in the art would appreciate that the entire drape 300, the outer envelope 1300, and the inside of the package 1200 may be sterile.

Figure 14A:
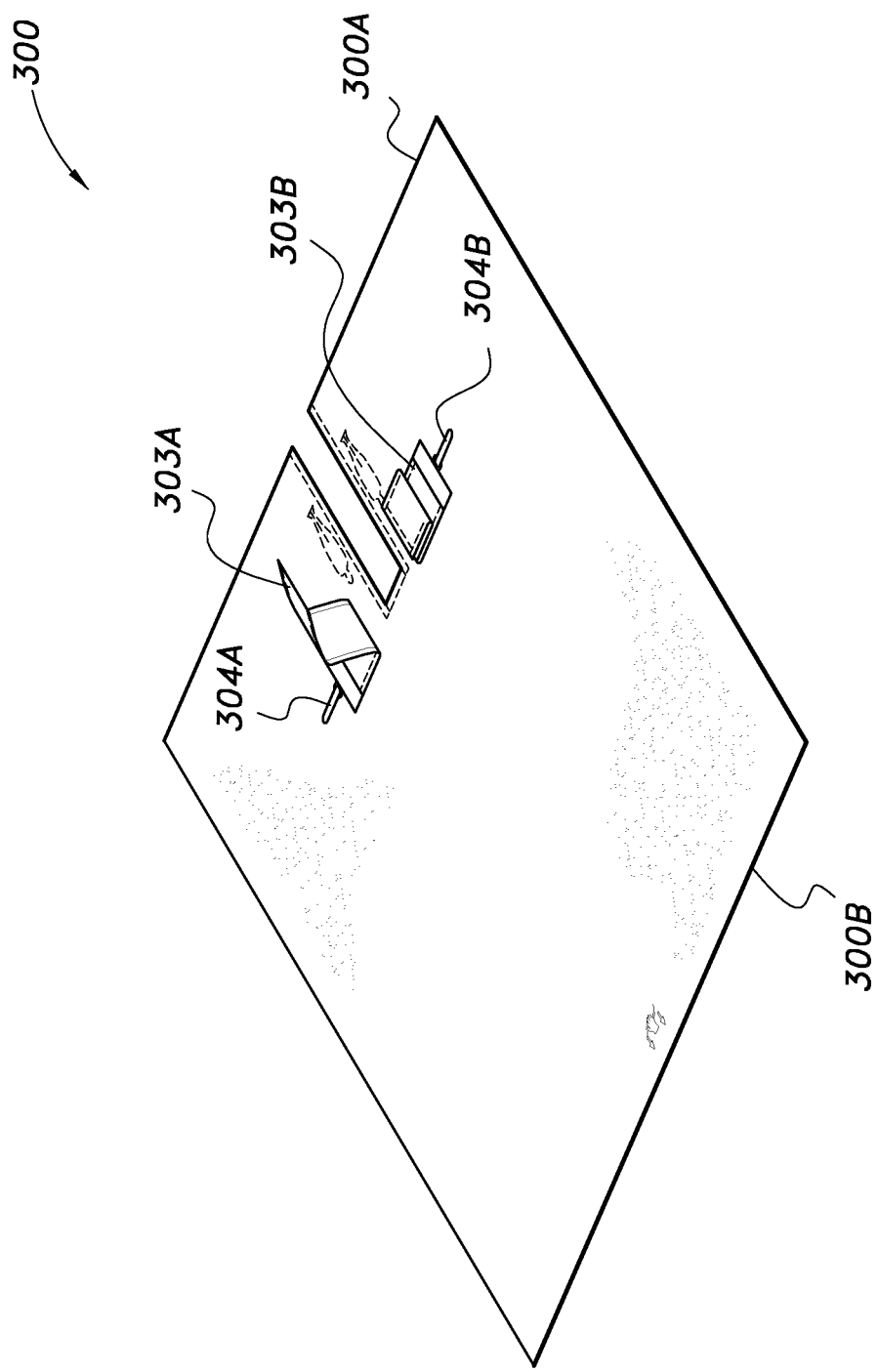
FIGS. 14A-14E represents a view of the top surface of an embodiment of the drape as it is being folded along the top surface of the drape.

Now one embodiment of the method of folding the drape 300 will be described with respect to FIGS. 14A-15C. These steps may be performed by a manufacturer of the drape or an end user of the drape. As shown in FIG. 14A, the drape 300 is positioned with its top surface facing a user. A preliminary step may include the user taping down the flaps 303A, 303B using sterile tape. A tri-fold of the flaps 303A, 303B is achieved by having the flaps 303A, 303B folded in a tri-fold fashion on the top surface 301 of the drape 300, and away from the sleeves 304A, 304B. Such that, folding of the flaps 303A, 303B results in the flaps 303A, 303B folding on themselves and they may not entirely cover or obstruct the sleeves 304A, 304B.

Figure 14B:
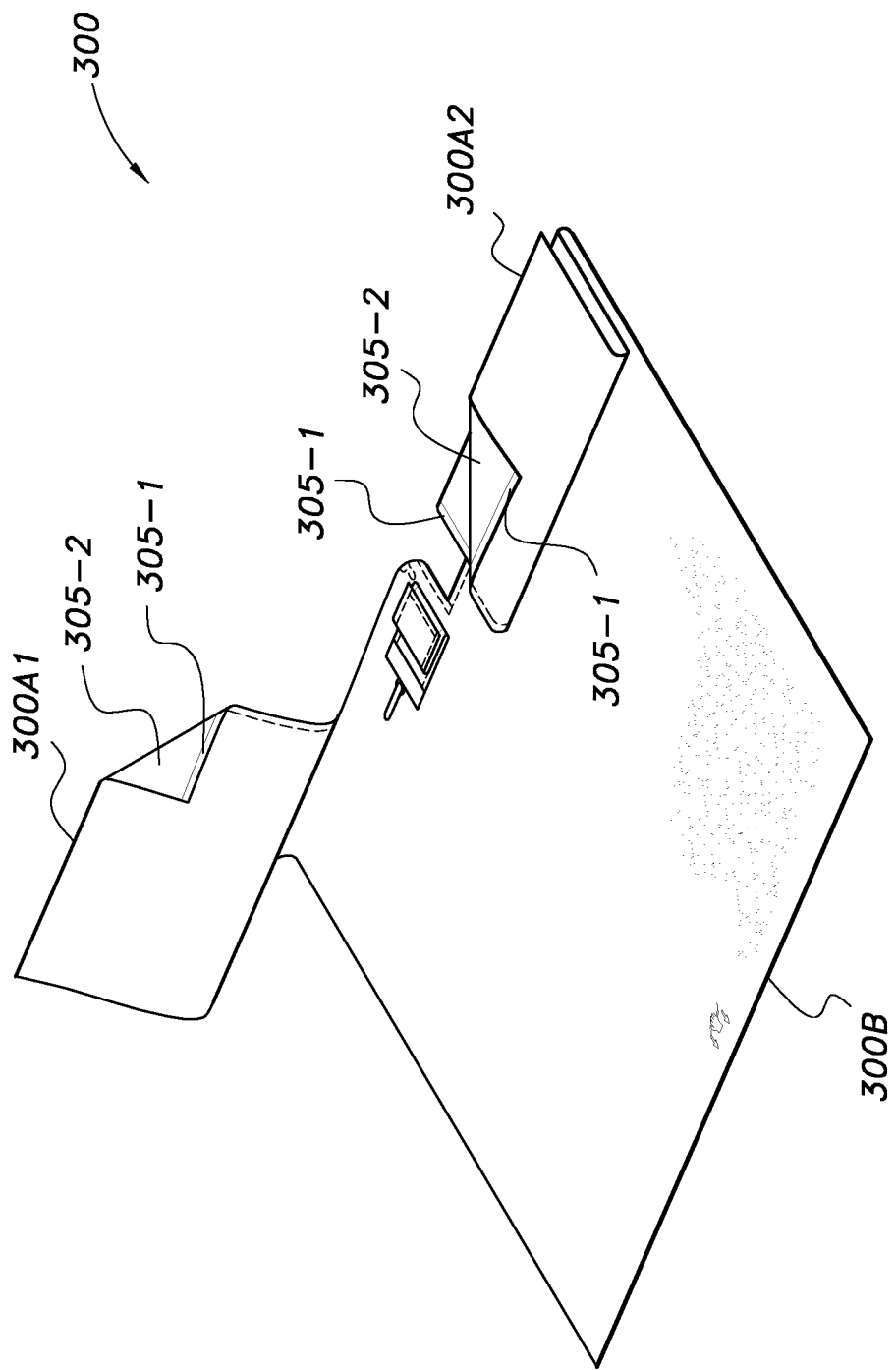

Next, as shown in an embodiment in FIG. 14B, the proximal most ends 300A1, 300A2 of the drape 300 may be folded in a three-fold fashion. This is achieved by first having the proximal most end 300A1 folded up to the flap 303A and then folding the proximal most end 300A1 back on itself. Similarly, the proximal most end 300A2 is folded up to the flap 303B and then folded back on itself. Thereby, folding the proximal most ends 300A1, 300A2 on the top surface 301 of the drape 300 in a three-fold fashion. The corners 305-2 of the proximal most ends 300A1, 300A2 are flipped back such that the bottom surface 306 of the drape 300 is exposed with the adhesive tape 305-1 along the u-shaped opening 305 faces the user.

Figure 14C:
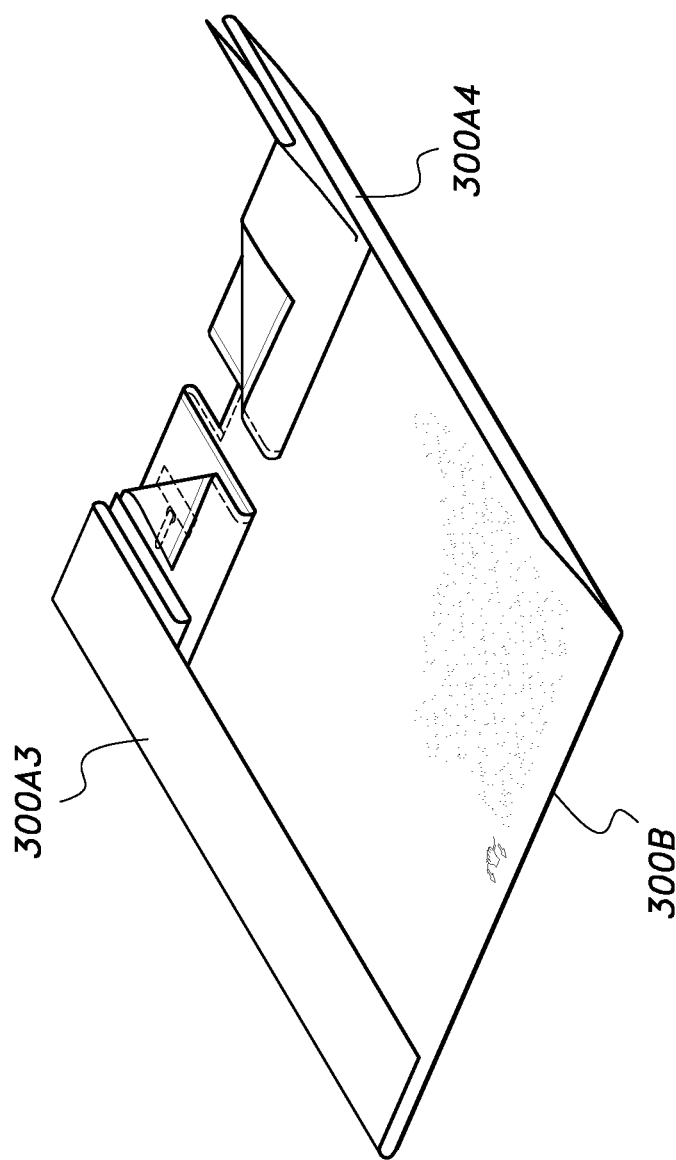
Figure 14D:
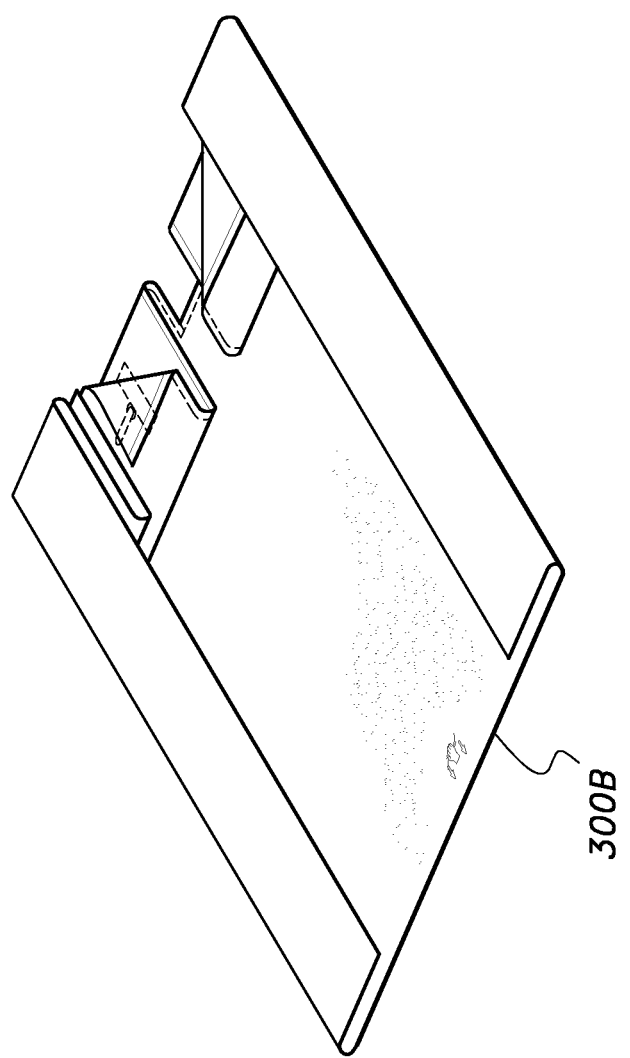

Now referring to another embodiment shown in FIG. 14C, the next step in the folding process of the drape 300 may include taking the ends 300A3, 300A4 of the drape 300 and folding them inward towards the center of the drape 300. The ends 300A3, 300A4 represent the right and left sides of the drape 300. During this folding procedure, the ends 300A3, 300A4 are brought in towards the center of the drape 300 up to the point where the flaps 303A, 303B are connected or attached to the top surface 301 of the drape 300. The folding of the ends 303A, 303B results in the final configuration as shown in an embodiment in FIG. 14D.

Next, multiple accordion folds may be done to the top surface 301 of the drape 300 such that the distal end 300B is placed on top of the proximal end 300A. The accordion folds are achieved by finding an approximate mid-point on the top surface 301 of the drape 300 and having the top surface 301 fold on itself in an accordion fashion such that the top surface 301 is stacked upon each other as shown in an embodiment in FIG. 14E. The stacking of the top surface 301 on top of each other is resultant of the accordion fold performed by the user to the top surface 301. It is important to note that after the accordion fold is completed, the distal end 300B of the drape 300 may be folded back on itself such that the top surface 301 of the drape 300 with the marking 302 is exposed to the user. The marking 302, as discussed above, may represent a hand symbol with direction of arrows that instruct a user, such as a physician, to pull the drape 300 in a certain direction.

Figure 15A:
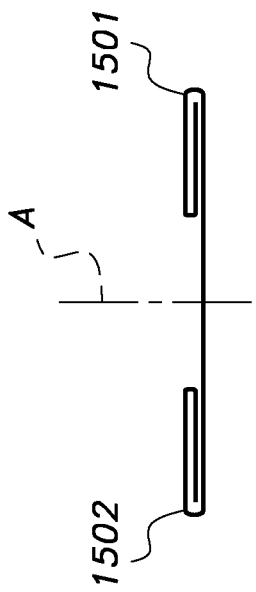
FIGS. 15A-15B represents folding of an embodiment of the drape in an accordion fashion and along a central axis of the drape.
Figure 15B:
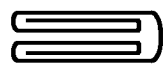
Figure 14E:
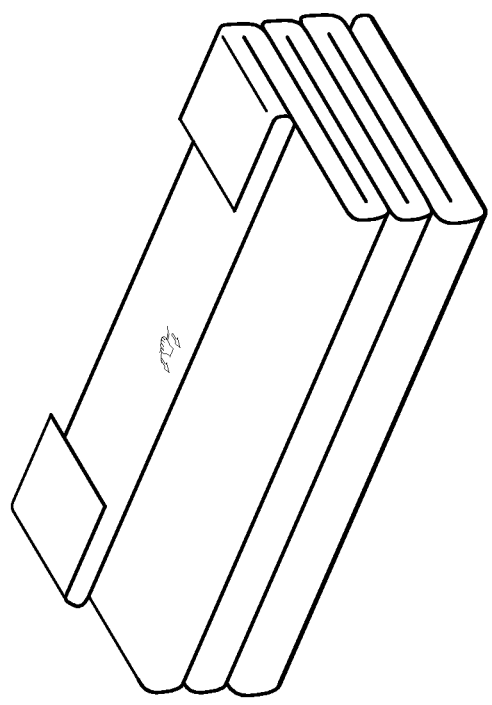

Now referring to an embodiment shown in FIG. 15A, the cross-section of the accordion folds as illustrated in FIG. 14E is shown. The next step is to have the ends 1501, 1502 of the drape 300 in the accordion fold to be folded towards each other, parallel to the top surface 301 of the drape 300 such that the ends 1501, 1502 meet at a central axis of the drape 300. The central axis of the drape 300A as shown in FIG. 15A is represented by "A". Lastly, and the final fold, is to have the ends 1501, 1502 folded toward each other along the central axis A in a book-like fashion as shown in FIG. 15B. Such a book-like configuration allows the drape 300 to be put together in a compact fashion that is easy to handle by the user. In this final configuration, shown in FIG. 15B, the adhesive tape 305-1A, 305-1B, 305-1C, on the bottom surface 306 of the drape 300 and the markings 307A, 307B are in view. The markings 307A, 307B inform the user on how to orient the drape 300 with respect to the patient.

In summary, FIGS. 14A-15B represents one example embodiment of an overall folding process of the drape 300 from start to finish such that the drape 300 can be packaged in a chevron pouch.

Now, an embodiment of the method of using the drape 300 (i.e., deploying the drape) will be described with reference to FIGS. 16A-F. Upon obtaining the package 1200 and after reading the instructions of use 1204, a user may open the package 1200, a chevron package. Upon disassembling the package 1200, the user may retrieve the folded drape with an outer envelope 1300 from the package 1200. At this point only the sterile portions (i.e., the bottom surface 306 of the drape 300) are in contact with the inner lining of the package 1200. In order to ensure that the sterile portions of the drape are not contaminated, the user follows close protocol in retrieving the folded drape 1300 out of the package 1200 and disassembling the same.

Figure 16A:
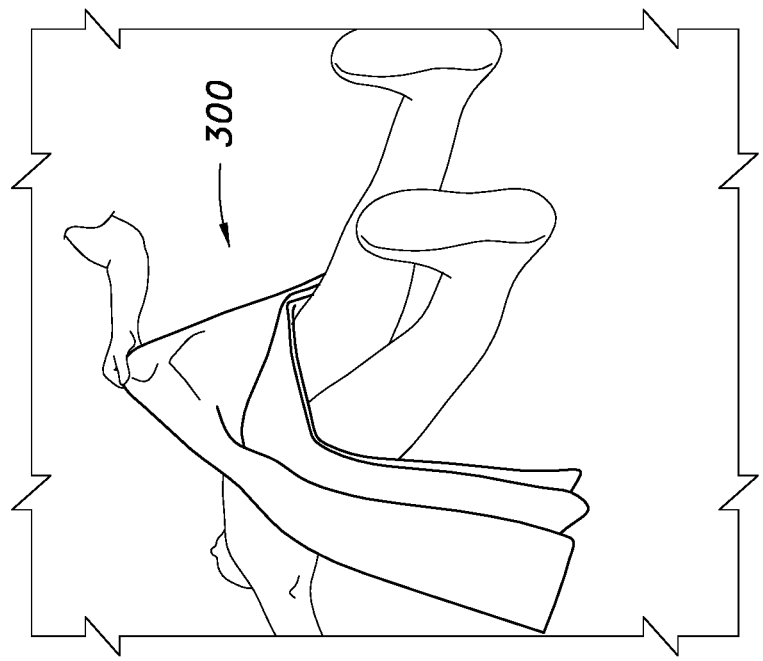
FIGS. 16A-16F represents the unfolding and deploying of an embodiment of the drape during a surgical procedure.

Once the drape 300 is unfolded, without contaminating the sterile top surface 301 of the drape 300, the user identifies the markings 307A, 307B on the bottom surface 306 of the drape 300. These markings 307A, 307B inform the user how to orient the drape 300 with respect to the patient. Upon identifying such markings 307A, 307B, the user aligns the u-shaped opening 305 of the drape 300 along the incision site of the patient's leg 108, as shown in FIG. 16A, such that the physician has a working space to make the desired incision as needed to perform the surgical procedure. After aligning the window cut-out or the u-shaped opening 305 along the incision site, the user may adhere the drape 300 to the patient using edge 305-1B of the tape along the edges of the u-shaped opening 305 on the back surface 306 of the drape 300. This step allows the drape 300 to be positioned in place and prevent it from being maneuvered or displaced during the deployment of the drape 300 before the tape strips around the edges 305-1A and 305-1C of the u-shaped opening 305 are used for final affixation to the patient. The user may then deploy the drape 300 by letting the ends 1501, 1502, as shown in FIG. 15A, to unfold. In other words, the folded ends 1501, 1502 are allowed to unfold along their respective direction in which they were folded.

Figure 16B:
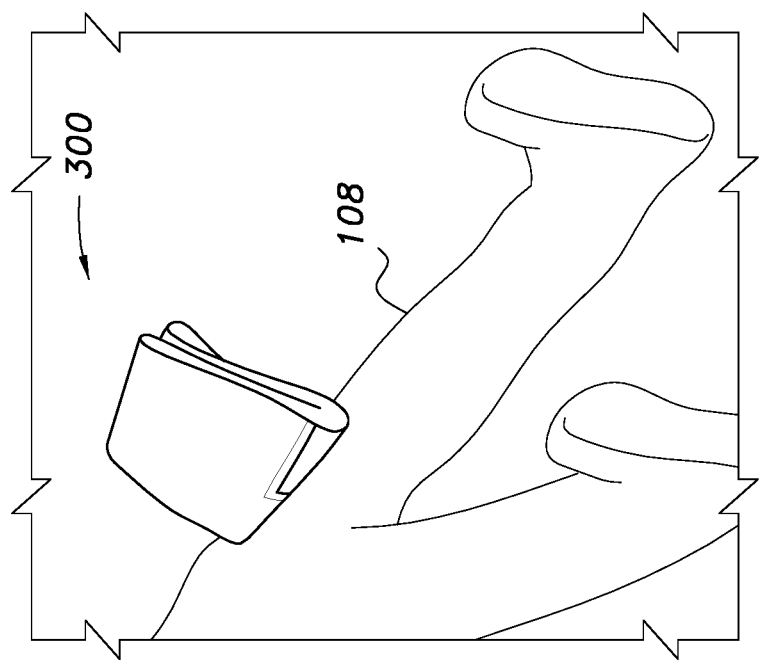
Figure 16D:
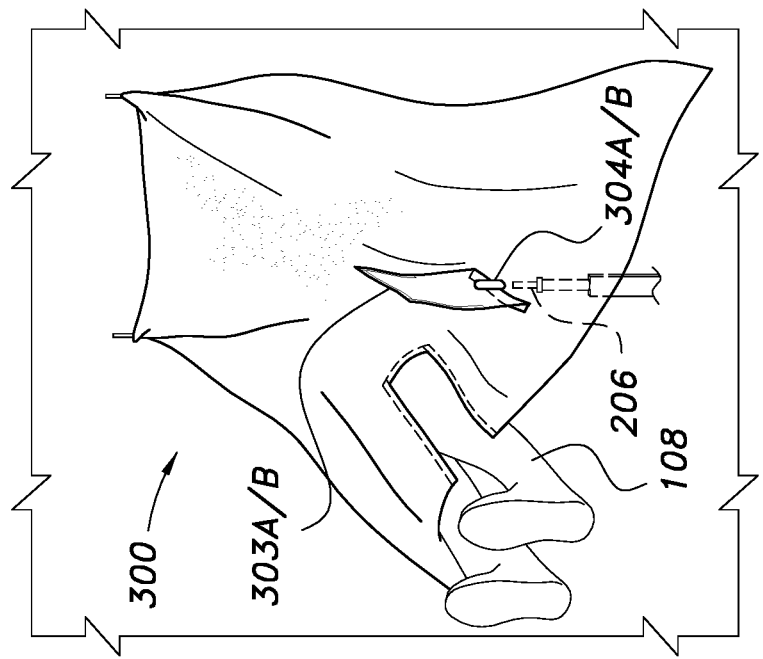
Figure 16C:
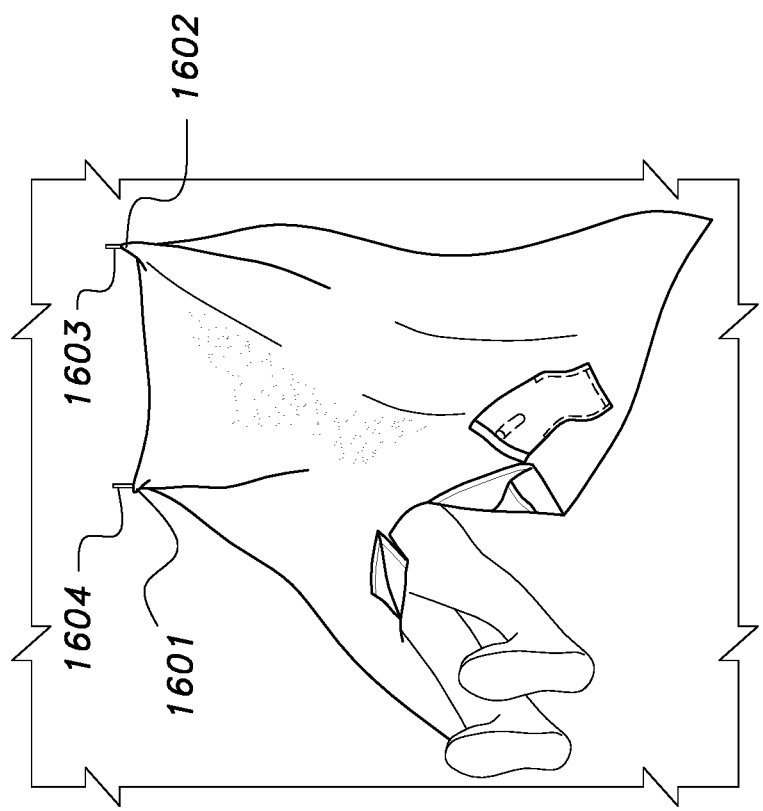

Thereafter, the user may identify the mark 302 on the top surface 301 which indicates to the user to pull the drape 300 in a certain direction. As shown in FIG. 16B, the distal end 300B of the drape 300 is pulled in a direction towards the patient's torso and head such that the bottom surface 306 of the drape 300 covers the patient. Next, as shown in an embodiment shown in FIG. 16C, two arbitrary points 1601, 1602 on the drape 300 may be identified and clipped onto two separate pins or hooks 1603, 1604. As shown in FIG. 16C, each point on the drape is connected or affixed to a respective pin or hook 1603, 1604. Thereafter, ends 300A3, 300A4 of the drape 300 are unfolded such that arms of the patient are covered or protected under the drape 300. And, ends 300A1, 300A2 of the drape 300 are unfolded to protect or cover at least a portion of the legs of the patient. Thereby, ensuring the u-shaped opening 305 is positioned on or around the incision site of the surgical procedure while the remaining portions of the drape cover the patient in order to maintain sterility and avoid contamination. As shown in an embodiment shown in FIG. 16D, the resulting configuration of the deployed drape 300 is achieved, wherein the bottom surface 306 of the drape 300 contacts the patient while the drape 300 is securely positioned and oriented by pins or hooks 1603, 1604, and the arms and legs of the patient are covered under the drape. In turn, ensuring sterility of the surgical site and the instruments used during the surgical procedure is maintained.

Next, the user may peel-off a protective outer covering of the adhesive tape 305-1A and 305-1C that runs along the edges of the u-shaped opening 305 from the bottom surface 306 of the drape 300. By peeling-off the protective outer covering, the adhesive sticky portion underneath the protective outer covering would be exposed which would allow the user to affix or firmly engage the drape 300, especially the u-shaped surgical opening 305, to the patient. One of ordinary skill in the art will appreciate that other methods of affixing the drape to the patient during unfolding may be used, either by using tape strips 305-1, or other sterile tape, or using a different sequence of taping and unfolding.

After having the drape 300 firmly engaged in its position and the u-shaped opening 305 in place around the surgical site of interest, the user may orient and/or fix the remaining portions of the drape 300 with respect to the surgical table 100.

Next, the user may engage the respective sleeve 304A, 304B with the post 206 depending on whether a surgical procedure is being performed on the right hip or the left hip. For example, if the right hip is being operated, as shown in FIG. 1, the second sleeve 304B is inserted or affixed to the square shaped post 206. Whereas, if the left hip is being operated on as shown in FIG. 16D, then the first sleeve 304A is inserted or affixed to the square shaped post 206. The inserting or affixing of the respective sleeve 304A, 304B on the post 206, with the use of handles 501A, 501B is described above with respect to FIGS. 5 and 6. Such inserting or affixing mechanism allows the drape 300 to be positioned in place with respect to the table 300, the femoral support hook 126 and the angled bracket 128. Thereby, ensuring that the drape 300 is in place and does not move or reposition during the surgical procedure.

Figure 16E:
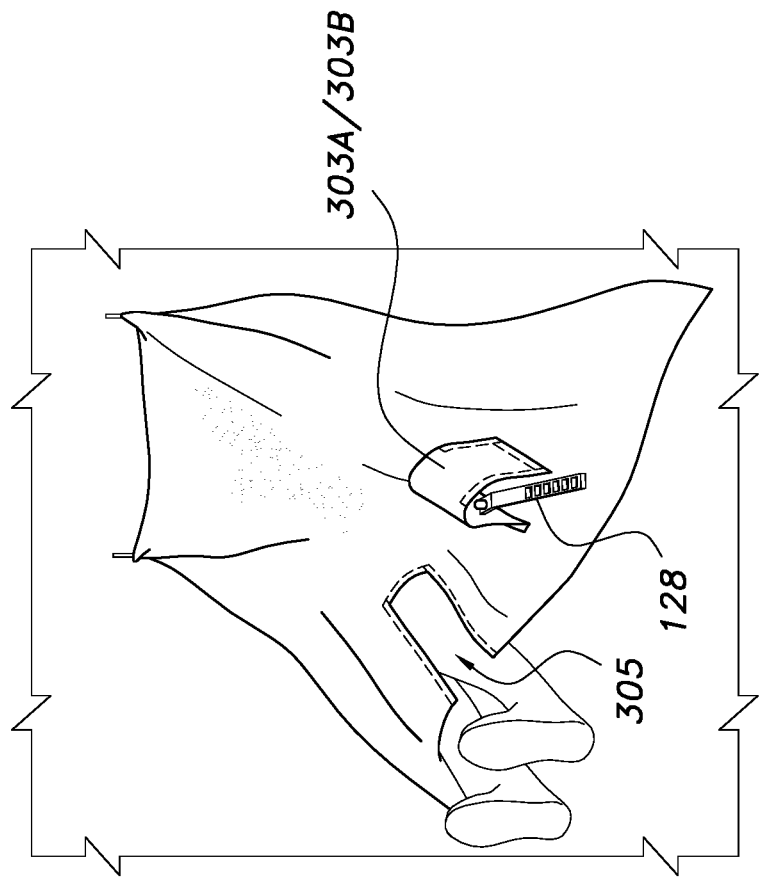
Figure 16F:
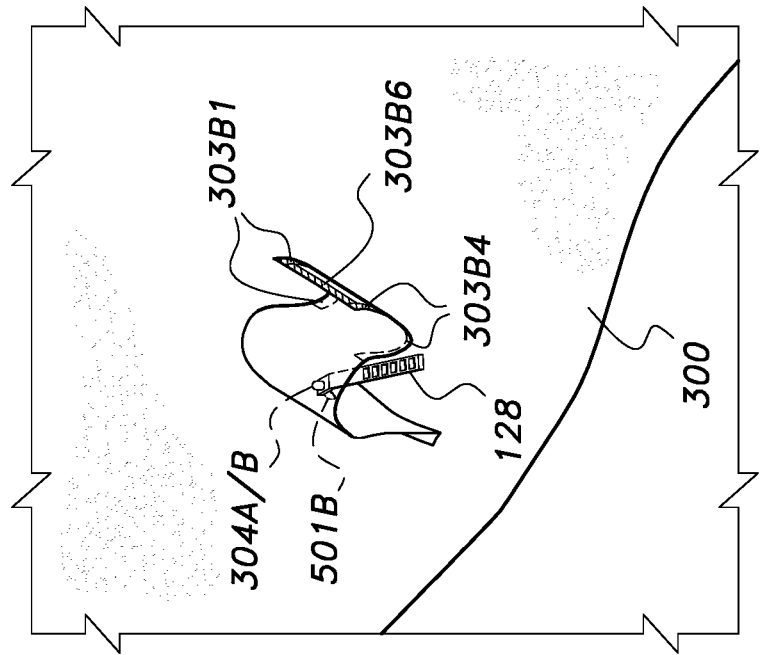

After the patient is fully draped and the drape 300 is securely engaged to the post 206, the user may then incorporate the sterile angled bracket 128 on top of the post 206, as shown in FIGS. 16E and 16F, thereby sandwiching and securely engaging the respective sleeve 304A, 304B between the post 206 and the angled bracket 128 and forming a sterile barrier between the post 206 and the angled bracket 128. After positioning the angled bracket 128, the respective flap 303A or 303B (depending which hip is being operated) is folded around the angled bracket 128 to act as a protective covering layer. For example, if the right hip is being operated on, as shown in FIG. 1, the second flap 303B is engaged by the user. Whereas, if the left hip is being operated on as shown in FIGS. 16E-16F, then the first flap 303A is engaged by the user. By engaging the first flap 303A or the second flap 303B, the user is essentially folding back the flap on itself as shown in further detail in FIG. 16F. As discussed above with respect to FIG. 8, in reference to the second flap 303B, the folding back of the second flap 303B results in the edge 303B4 folding back on itself to form a second barrier on the drape 300 and the angled bracket 128 as the adhesive tape on the edge 303B4 attaches to itself and to the drape 300. It is noted that only one flap 303A or 303B may be used for any one procedure. After the fold, the portion or edge 303B5 is adjacent to the end of the bracket 128 nearest the post 206. In certain embodiments, edge 303B5 does not include adhesive so that the bracket 128 can rotate about the post 206 during the surgical procedure without being restricted by the flap 303B. The edge 303B1 folds back on itself to form a second barrier on the angled bracket 128 and the drape 300 as the adhesive tape on the edge 303B1 attaches to the drape 300, and the adhesive tape on the edge 303B6 attaches to the drape 300. Similarly, after the fold, the section 303B2 is adjacent to the distal end of bracket 128, and does not include adhesive so that the bracket 128 can rotate about the post 206 during the surgical procedure without being restricted by the flap 303B.

Such a folding and taping configuration allows an additional barrier layer of protection to be formed on the angled bracket 128 and the top surface 301 of the drape 300. This ensures maintaining sterility and preventing or at least minimizing contamination. The sleeve 304A or 304B covers the post 206, and the flap 303A or 303B provides an additional protective barrier between the post 206 and the surgical procedure, for example, in case of a rip or tear in the sleeve 304A or 304B.

Thereafter, femoral support hook 126 is installed into an appropriate opening on the angled bracket 128. Both, the femoral support hook 126 and the angled bracket 128 are sterilized prior to each procedure. The femoral support hook 126 is a Food and Drug Administration (FDA) class 2 device as it contacts and supports the patient's femur bone. As discussed above with respect to FIG. 2, a user is able to drive the femur lift mechanism or jack 124 up and down in order to adjust the elevation of the femoral support hook 126.

Such unfolding and placement mechanism of the drape onto the table and surgical site ensures that the sterile segments of the drape and equipment used for the surgical procedure remain sterile, and are not contaminated by the non-sterile segments.

It will be appreciated by those skilled in the art that changes could be made to the embodiments described above without departing from the broad inventive concept thereof. For example, various mechanical and electrical connection elements and actuators can be used to achieve the disclosed function. It is understood, therefore, that this invention is not limited to the particular embodiments disclosed, but it is intended to cover modifications within the spirit and scope of the present invention as defined by the appended claims.

What is claimed is:

1. A drape for use in a surgical procedure, comprising:
a top surface and an opposite bottom surface;
at least one sleeve extending away from the top surface of the drape; and
at least one flap extending away from the top surface of the drape, the at least one flap and the at least one sleeve are by a proximal end of the top surface of the drape,
wherein the at least one flap comprises a first height and the at least one sleeve comprises a different second height, wherein the first height is greater than the second height such that the at least one flap extends beyond a length of the at least one sleeve when both the at least one flap and the at least one sleeve are in an extended configuration.

2. The drape of claim 1, wherein the at least one flap includes a front side and a back side, wherein the back side includes an adhesive tape positioned on at least one edge of the back side.

3. The drape of claim 2, wherein the at least one edge of the back side of the at least one flap includes a first edge and a different second edge, and the adhesive tape is positioned on the first edge and includes a first length, wherein the adhesive tape is positioned on the second edge and includes a second length, and wherein the first length is greater than the second length.

4. The drape of claim 3, wherein,
the adhesive tape positioned on the first edge is configured to fold back on itself to form a barrier on the drape.

5. The drape of claim 1, wherein,
the at least one flap is secured at an edge of the top surface of the drape, and the at least one flap is configured to form a barrier by wrapping around a first device and the at least one sleeve while the at least one sleeve is engaged with a surgical table, and
the at least one sleeve comprises an opening accessible from a bottom surface of the drape to an interior of the at least one sleeve, wherein the opening of the at least one sleeve comprises a closed end opposite the opening accessible from the bottom surface of the drape, and wherein the opening of the at least one sleeve is configured to receive a second device, wherein the second device is configured to engage with the first device prior to the at least one flap being configured to form the barrier.

6. The drape of claim 5, wherein the first device is a femoral support hook.

7. The drape of claim 5, wherein the second device is a femur lift.

8. The drape of claim 5, further comprising:
a first opening configured to correspond to an incision site on the proximal end of the drape, wherein the first opening is positioned between a first sleeve and a different second sleeve,
wherein the bottom surface of the drape includes at least one marking, wherein the at least one marking is configured to identify a position of a patient relative to the drape, and wherein the at least one marking is positioned by the proximal end of the drape, and
wherein the first device is a femoral support hook.

9. The drape of claim 1, further comprising:
a first opening configured to correspond to an incision site on the proximal end of the drape, the first opening positioned between a first sleeve and a different second sleeve.

10. The drape of claim 9, wherein,
the at least one flap is positioned between the at least one sleeve and the first opening, and
the at least one flap is configured to obstruct the at least one sleeve from the first opening.

11. The drape of claim 1, wherein,
the at least one flap includes a first flap and a different second flap, wherein the first flap is spaced apart from the second flap on the top surface of the drape,
the at least one sleeve includes a first sleeve and a different second sleeve, wherein the first sleeve is spaced apart from the second sleeve on the top surface of the drape, and
the first flap is positioned adjacent to the first sleeve and the second flap is positioned adjacent to the second sleeve.

12. The drape of claim 11, wherein,
the first flap includes a first height and the first sleeve includes a second height, wherein the first height is greater than the second height, and
the second flap includes a third height and the second sleeve includes a fourth height, wherein the third height is greater than the fourth height.

13. The drape of claim 1, wherein the at least one sleeve includes at least one projection extending from a base of the at least one sleeve to a first free end, wherein the first free end is configured to be engaged by a user for maneuvering the at least one sleeve over a second device.

14. The drape of claim 1, wherein,
the at least one sleeve includes a first sleeve and a different second sleeve, the first sleeve is spaced apart from the second sleeve on the top surface of the drape, and
the first sleeve includes a first opening that extends from the bottom surface of the drape to a first interior of the first sleeve,
the second sleeve includes a second opening that extends from the bottom surface of the drape to a second interior of the second sleeve, and
the first sleeve is configured to be placed on a second device, and the second sleeve is configured to be placed on a third device.

15. The drape of claim 1, wherein the drape includes at least one marking on the bottom surface of the drape, wherein the at least one marking is configured to identify a position of a user relative to the drape, the at least one marking positioned by the proximal end of the drape.

16. The drape of claim 1, further comprising:
a first opening configured to correspond to an incision site, the first opening being in a U-shape configuration.

17. The drape of claim 1, wherein the bottom surface of the drape is configured to contact a first user being a patient, the top surface of the drape is configured to engage with a second user being one of a physician and a technician, the top surface and the bottom surface extending between the proximal end and a distal end of the drape.

18. A method of packaging a drape, comprising:
folding the drape, the drape comprising:
a top surface and an opposite bottom surface;
at least one sleeve extending away from the top surface of the drape;
at least one flap extending away from the top surface of the drape, the at least one flap and the at least one sleeve are by a proximal end of the top surface of the drape; and
wherein the at least one flap comprises a first height and the at least one sleeve comprises a different second height, wherein the first height is greater than the second height such that the at least one flap extends beyond a length of the at least one sleeve when both the at least one flap and the at least one sleeve are in an extended configuration.

19. The method of claim 18, wherein the drape further includes a first opening configured to correspond to an incision site, wherein the first opening is a U-shape configuration.

20. The method of claim 18, wherein,
the at least one flap is secured at an edge of the top surface of the drape, and the at least one flap is configured to form a barrier by wrapping around a first device and the at least one sleeve while the at least one sleeve is engaged with a surgical table, and
the at least one sleeve comprises an opening accessible from a bottom surface of the drape to an interior of the at least one sleeve, wherein the opening of the at least one sleeve comprises a closed end opposite the opening accessible from the bottom surface of the drape, and wherein the opening of the at least one sleeve is configured to receive a second device, wherein the second device is configured to engage with the first device prior to the at least one flap being configured to form the barrier, and
the bottom surface of the drape is configured to contact a first user being a patient, the top surface of the drape is configured to engage with a second user being one of a physician and a technician, the top surface and the bottom surface extending between the proximal end and a distal end of the drape.

* * * * *